(12) United States Patent
Srinivasan et al.

(10) Patent No.: US 11,213,633 B2
(45) Date of Patent: Jan. 4, 2022

(54) PEN NEEDLE MAGAZINE

(71) Applicant: Becton, Dickinson and Company, Franklin Lakes, NJ (US)

(72) Inventors: Sudarsan Srinivasan, North Brunswick, NJ (US); Cole Constantineau, Cambridge, MA (US); Michel Bruehwiler, Newton, MA (US); Tyson Montidoro, Davie, FL (US); Jeffrey Chagnon, Somerville, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 583 days.

(21) Appl. No.: 16/095,080

(22) PCT Filed: Mar. 31, 2017

(86) PCT No.: PCT/US2017/025300
§ 371 (c)(1),
(2) Date: Oct. 19, 2018

(87) PCT Pub. No.: WO2017/189166
PCT Pub. Date: Nov. 2, 2017

(65) Prior Publication Data
US 2019/0111215 A1  Apr. 18, 2019

Related U.S. Application Data

(60) Provisional application No. 62/328,666, filed on Apr. 28, 2016.

(51) Int. Cl.
*A61M 5/32* (2006.01)
*A61M 5/24* (2006.01)
(Continued)

(52) U.S. Cl.
CPC ........ *A61M 5/3298* (2013.01); *A61M 5/2466* (2013.01); *A61M 5/3202* (2013.01);
(Continued)

(58) Field of Classification Search
CPC .............. A61M 5/2466; A61M 5/3298; A61M 5/3202; A61M 5/3295; A61M 2005/0047; A61M 2005/2474; A61M 5/347
See application file for complete search history.

(56) References Cited

U.S. PATENT DOCUMENTS 5,829,589 A   11/1998 Nguyen et al.
5,873,462 A    2/1999 Nguyen et al.
(Continued)

FOREIGN PATENT DOCUMENTS

EP    2119423 A1   11/2009
EP    2420270 A2    2/2012
(Continued)

OTHER PUBLICATIONS

Li-Yuan Chang et al., "Integrated Flow Sensing for Focal Biochemical Stimulation", Proceedings of the Third IEEE International Conference on Nano/Micro Engineered and Molecular Systems, Jan. 6-9, 2008, Sanya, China, pp. 921-926, (6 Pages Total).

*Primary Examiner* — Laura A Bouchelle
(74) *Attorney, Agent, or Firm* — Dickinson Wright PLLC

(57) ABSTRACT

An attachable needle assembly (2) for use on a medication delivery pen (4), the needle assembly (2) comprising a housing (16) that engage the medication delivery pen (4), the housing (16) enclosing a plurality of needles (34) that pierce a reservoir septum (6) of the medication delivery pen (4), a plurality of needle posts (24) each securing one of the plurality of needles (34), and a needle assembly septum (60) enclosing the plurality of needles (34). The needle assembly (2) further including a plurality of integrated peel tabs (70)
(Continued)

each detachably connected to one of the plurality of needle posts (24), wherein in a first position of the needle assembly (2), the plurality of needles (34) is disposed in the needle assembly septum (60), and in a second position of the needle assembly (2), one of the plurality of integrated peel tabs (70) is drawn out of the housing (16) to cause a selected needle (40) of the plurality of needles (34) to pierce the needle assembly septum (60) and be exposed for medication delivery.

18 Claims, 12 Drawing Sheets

(51) Int. Cl.
*A61M 5/34* (2006.01)
*A61M 5/00* (2006.01)

(52) U.S. Cl.
CPC .......... *A61M 5/3293* (2013.01); *A61M 5/347* (2013.01); *A61M 2005/004* (2013.01); *A61M 2005/2474* (2013.01)

(56) References Cited

U.S. PATENT DOCUMENTS

| | | | |
|---|---|---|---|
| 5,931,817 | A | 8/1999 | Nguyen et al. |
| 8,876,780 | B2 | 11/2014 | Bruehwiler et al. |
| 9,101,724 | B2 | 8/2015 | Chapin et al. |
| 9,107,988 | B2 | 8/2015 | Bruehwiler et al. |
| 9,155,838 | B2 | 10/2015 | Bilton et al. |
| 9,381,303 | B2 | 7/2016 | Abhijitsinh et al. |
| 9,427,514 | B2 * | 8/2016 | Bruehwiler ......... A61M 5/3205 |
| 9,717,860 | B2 | 8/2017 | Bruehwiler et al. |
| 10,029,042 | B2 | 7/2018 | Searle et al. |
| 2001/0014792 | A1 | 8/2001 | West et al. |
| 2002/0020646 | A1 | 2/2002 | Groth et al. |
| 2002/0020647 | A1 | 2/2002 | Groth |
| 2005/0084631 | A1 | 4/2005 | Anderson |
| 2008/0312604 | A1 | 12/2008 | Boesen |
| 2010/0152660 | A1 | 6/2010 | Mack et al. |
| 2010/0217206 | A1 | 8/2010 | Lum et al. |
| 2011/0068034 | A1 | 3/2011 | Hwang et al. |
| 2012/0004620 | A1 | 1/2012 | Spool et al. |
| 2012/0016315 | A1 | 1/2012 | Radmer et al. |
| 2012/0041373 | A1 | 2/2012 | Bruehwiler et al. |
| 2012/0041381 | A1 | 2/2012 | Raj et al. |
| 2012/0041383 | A1 | 2/2012 | Bruehwiler et al. |
| 2012/0041390 | A1 | 2/2012 | Spool et al. |
| 2012/0130313 | A1 | 5/2012 | Byerly et al. |
| 2013/0041321 | A1 | 2/2013 | Cross et al. |
| 2013/0053751 | A1 | 2/2013 | Holtham |
| 2014/0076758 | A1 | 3/2014 | Dasbach et al. |
| 2014/0123479 | A1 | 5/2014 | Dasbach |
| 2014/0262884 | A1 | 9/2014 | Priebe et al. |
| 2014/0299622 | A1 | 10/2014 | Hofmann et al. |
| 2014/0339113 | A1 | 11/2014 | Hofmann et al. |
| 2015/0025469 | A1 | 1/2015 | Larsen et al. |
| 2015/0163898 | A1 | 6/2015 | Mokhtarzad |
| 2015/0335827 | A1 | 11/2015 | Stefansen et al. |
| 2015/0346184 | A1 | 12/2015 | Galasso |
| 2016/0000992 | A1 | 1/2016 | Steel et al. |
| 2016/0030683 | A1 | 2/2016 | Taylor et al. |
| 2016/0074587 | A1 | 3/2016 | Searle et al. |
| 2016/0082195 | A1 | 3/2016 | Atterbury et al. |
| 2016/0106925 | A1 | 4/2016 | Boesen |
| 2017/0106136 | A1 | 4/2017 | DiBiasi |

FOREIGN PATENT DOCUMENTS

| | | |
|---|---|---|
| EP | 2586475 A1 | 5/2013 |
| EP | 2696913 B1 | 9/2015 |
| JP | 2013544153 | 12/2013 |
| WO | 2008/150715 A1 | 12/2008 |
| WO | WO-2011083055 A1 | 7/2011 |
| WO | 2014/020001 A1 | 2/2014 |
| WO | 2015191457 A1 | 12/2015 |
| WO | 2016/050902 A1 | 4/2016 |

* cited by examiner

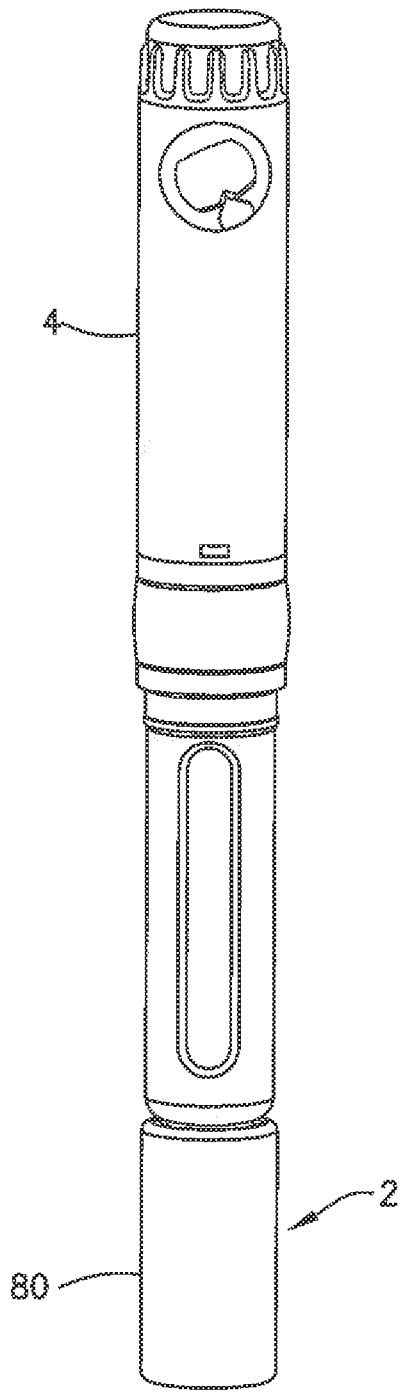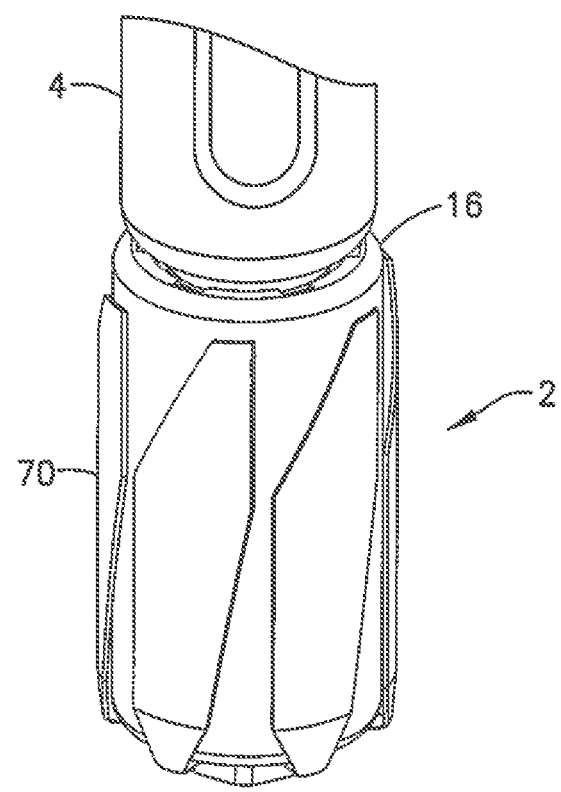
FIG.1
FIG.2

PEN NEEDLE MAGAZINE

This application claims the benefit under 35 U.S.C. § 119(e) of U.S. Provisional Patent Application Ser. 62/328,666, filed on Apr. 28, 2016, which is hereby incorporated by reference in its entirety.

FIELD

Various exemplary embodiments of the invention relate to medication pens.

BACKGROUND

Medication pens are typically used to inject medication into a patient. A person who must periodically self-inject doses of medication will typically carry a medication pen and several single-use pen needles. A medication pen is designed for safety and sterility. However, inefficiencies and inconveniences arise.

SUMMARY OF THE INVENTION

It is an aspect of the present invention to provide a needle assembly that is attachable to a medication delivery pen to provide a magazine of needles for use. Such a needle assembly provides advantages in separating a patient end and a non-patient end, and allows for engagement and disengagement to the medication delivery pen. Moreover, improvements in sterility, simplicity and safety are achieved by the needle assembly because all of the needles in the magazine pierce the septum of the medication delivery pen throughout operation, each needle only moves axially, and the needles are unable to be reused.

Needle reuse is undesired for at least the following reasons. The needle dulls after a single use and so subsequent use may cause pain to the patient. Multiple needle use can also reduce the strength of the needle tip which may cause a potential fracture. Also, needle reuse increases sanitary concerns and health risks to the patient.

The needle assembly of the present invention advantageously reduces reuse for at least the following reasons. Although patients may desire to financially benefit from using a needle multiple times, the needle assembly is configured to prevent each of the plurality of needles from being used more than once. Convenience is another reason patients reuse needles. Patients may also be concerned about not having another needle available for use or not having access to supplies. However, the needle assembly conveniently provides multiple needles so that an unused needle is more readily available.

The foregoing and/or other aspects of the present invention can be achieved by providing an attachable needle assembly for use on a medication delivery pen, the needle assembly comprising a housing configured to engage the medication delivery pen, the housing enclosing a plurality of needles configured to pierce a reservoir septum of the medication delivery pen, a plurality of needle posts each securing one of the plurality of needles, and a needle assembly septum enclosing the plurality of needles. The needle assembly further including a plurality of integrated peel tabs each detachably connected to one of the plurality of needle posts, wherein in a first position of the needle assembly, the plurality of needles is disposed in the needle assembly septum, and in a second position of the needle assembly, one of the plurality of integrated peel tabs is drawn out of the housing to cause a selected needle of the plurality of needles to pierce the needle assembly septum and be exposed for medication delivery.

The foregoing and/or other aspects of the present invention can also be achieved by a method of operating an attachable needle assembly on a medication delivery pen, the method comprising piercing a reservoir septum of the medication delivery pen with a plurality of needles, engaging the medication delivery pen with a housing enclosing the plurality of needles, securing each of the plurality of needles to one of a plurality of needle posts, disposing the plurality of needles in a needle assembly septum, and connecting a plurality of integrated peel tabs to each of the plurality of needle posts, wherein in a first position of the needle assembly, the plurality of needles is disposed in the needle assembly septum, and in a second position of the needle assembly, one of the plurality of integrated peel tabs is drawn out of the housing to cause a selected needle of the plurality of needles to pierce the needle assembly septum.

Additional and/or other aspects and advantages of the present invention will be set forth in the description that follows, or will be apparent from the description, or may be learned by practice of the invention.

BRIEF DESCRIPTION OF THE DRAWINGS

The above aspects and features of the present invention will be more apparent from the description for the exemplary embodiments of the present invention taken with reference to the accompanying drawings, in which:

FIG. 1 illustrates a right side elevation view of an exemplary medication delivery pen connected to a needle assembly;

FIG. 2 illustrates a front elevation view of the medication delivery pen connected to the needle assembly with a cover removed;

DETAILED DESCRIPTION OF EXEMPLARY EMBODIMENTS

Figure 3:
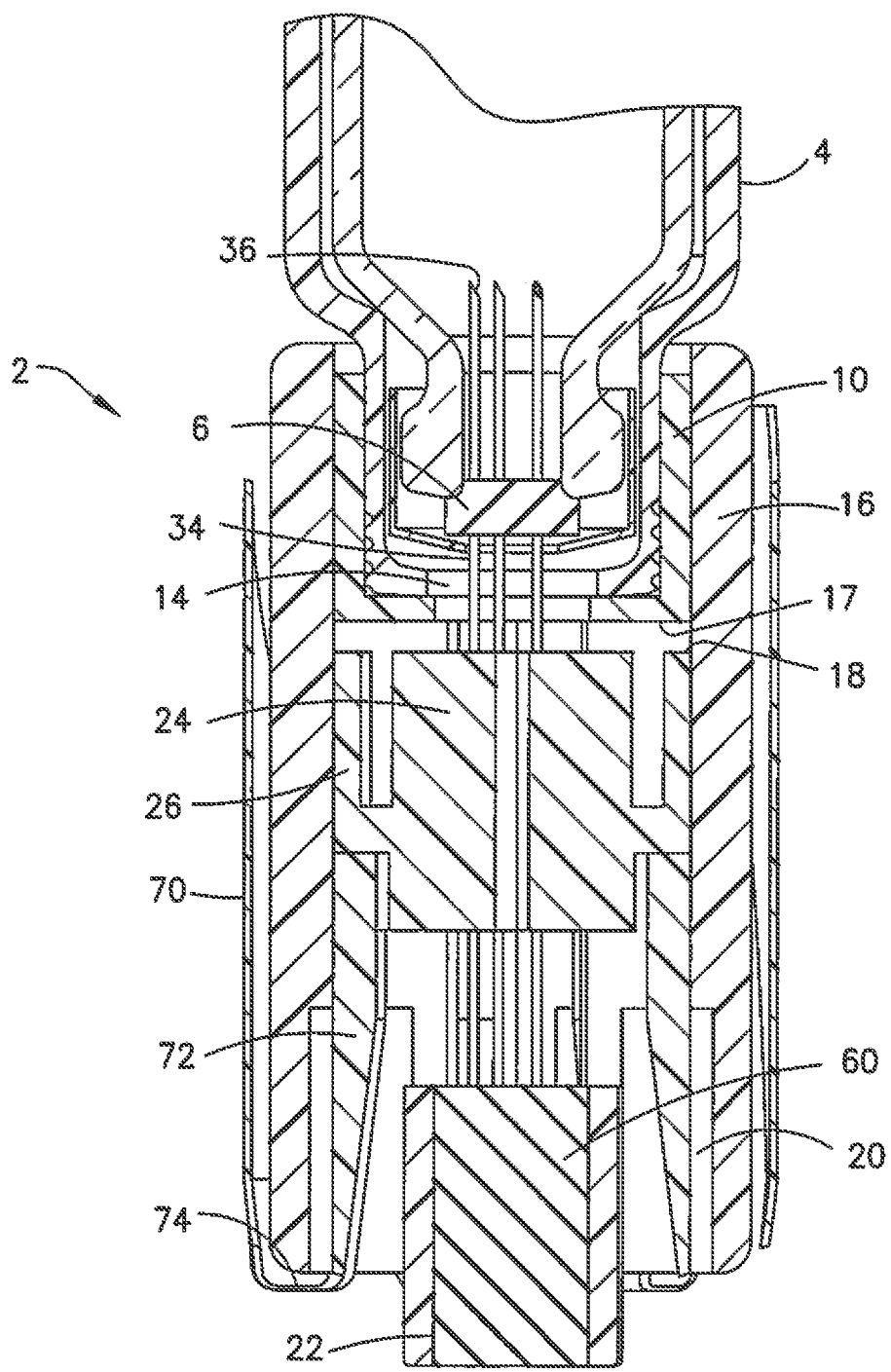
FIG. 3 illustrates a cross sectional view of a first position of the needle assembly.

FIG. 1 illustrates a medication delivery pen 4 used for injecting medicament, such as liquid drugs, into a living body. A needle assembly 2, enclosed by a removable cover 80, is mounted on the medication delivery pen 4 to enhance medication delivery. FIG. 2 illustrates the removable cover 80 that encloses the needle assembly 2 being removed. Specifically, the needle assembly 2 includes a main housing 16 and a plurality of integrated peel tabs 70 wrapped around the main housing 16. Benefits and advantages of the needle assembly 2 are described below.

According to one embodiment, FIG. 3 illustrates a cross sectional view of a first position of the needle assembly 2 where none of a plurality of needles 34 are exposed for medicament delivery. The needle assembly 2 preferably includes a magazine of six hollow needles 34, although greater or fewer needles are contemplated.

Figure 11:
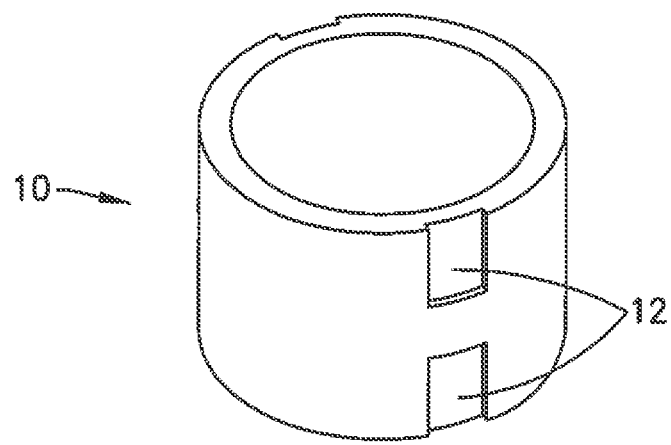
FIG. 11 illustrates a right perspective view of a needle hub.

The needle assembly 2 includes a needle hub 10 having mounting grooves 12 and an opening 14. As illustrated in FIG. 11, the mounting grooves 12 are located on an outer diameter of the needle hub 10 and are configured to engage an inner diameter of the main housing 16. An inner diameter of the needle hub 10 includes threads (not shown). The threads of the needle hub 10 are configured to engage the medication delivery pen 4. Although threads are the preferred engagement means between the needle hub 10 and the medication delivery pen 4, various other engagement means are contemplated.

The opening 14 allows the plurality of needles 34 to pass through. The plurality of needles 34 establishes fluid communication between the needle assembly 2 and the medication delivery pen 4. Specifically, a sharpened proximal end 36 of each needle 34 is configured to pierce a vial, cartridge or reservoir septum 6, for example, of the medication delivery pen 4 and establish fluid communication between the liquid medication-containing vial, cartridge or reservoir and the needle assembly 2. The needle hub 10 is advantageously separate from the main housing 16 and the medication delivery pen 4 so that when the needle assembly 2 is attached to the medication delivery pen 4, the plurality of needles 34 do not rotate.

It is important that the plurality of needles 34 do not rotate as the needle assembly 2 is being attached to the medication delivery pen 4. To avoid rotation of the plurality of needles 34, the needle assembly 2 is configured so that the needle hub 10 rotates with respect to the plurality of needles 34 to attach to the medication delivery pen 4. Specifically, a main housing 16 is split into a top portion and a bottom portion. When the needle assembly 2 attaches to the medication delivery pen 4, the top of the main housing 16 torques the needle hub 10 but does not torque the plurality of needles 34. The top portion of the main housing 16 is fixed axially but free rotationally with respect to the bottom portion of the main housing 16. The bottom portion of the main housing 16 is aligned (or keyed) to the needle hub 10.

Figure 12:
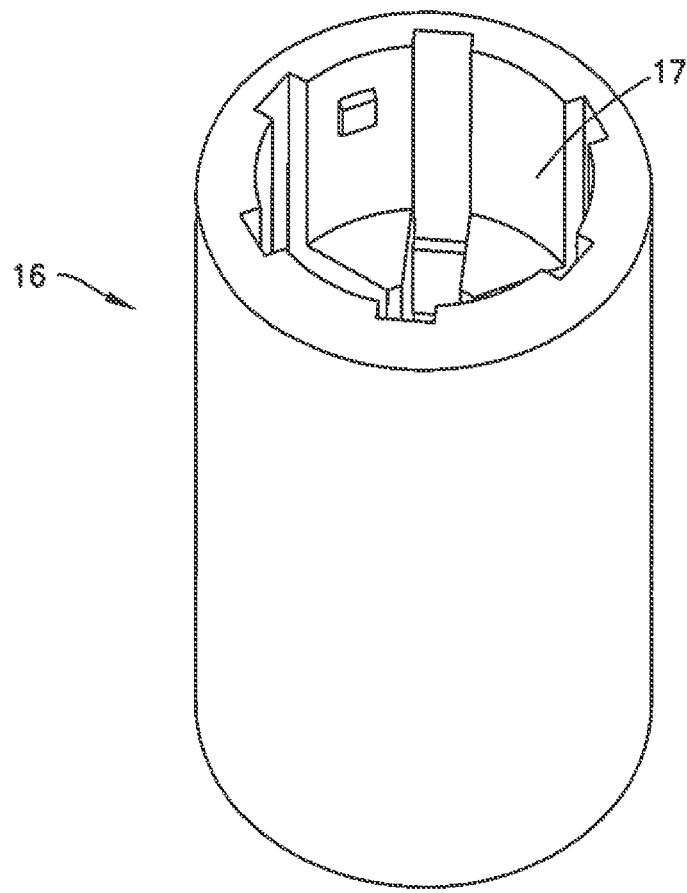
FIG. 12 illustrates a right perspective view of a main housing.
Figure 13:
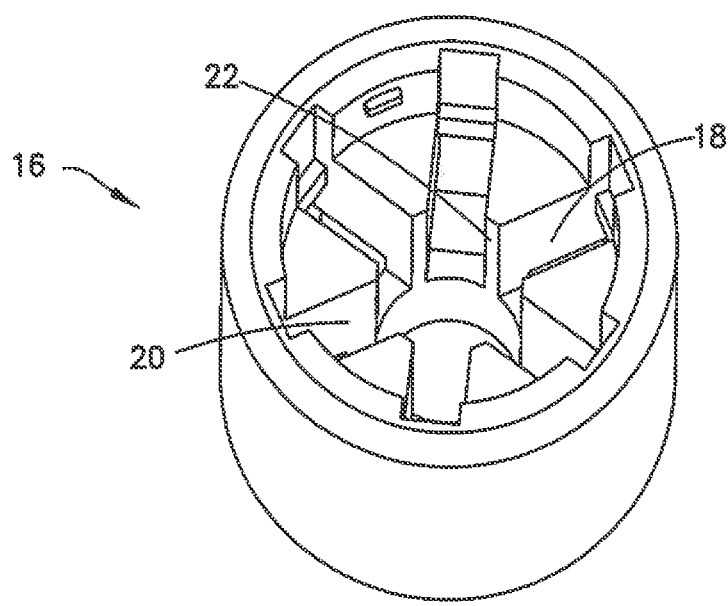
FIG. 13 illustrates a top perspective view of the main housing.
Figure 14:
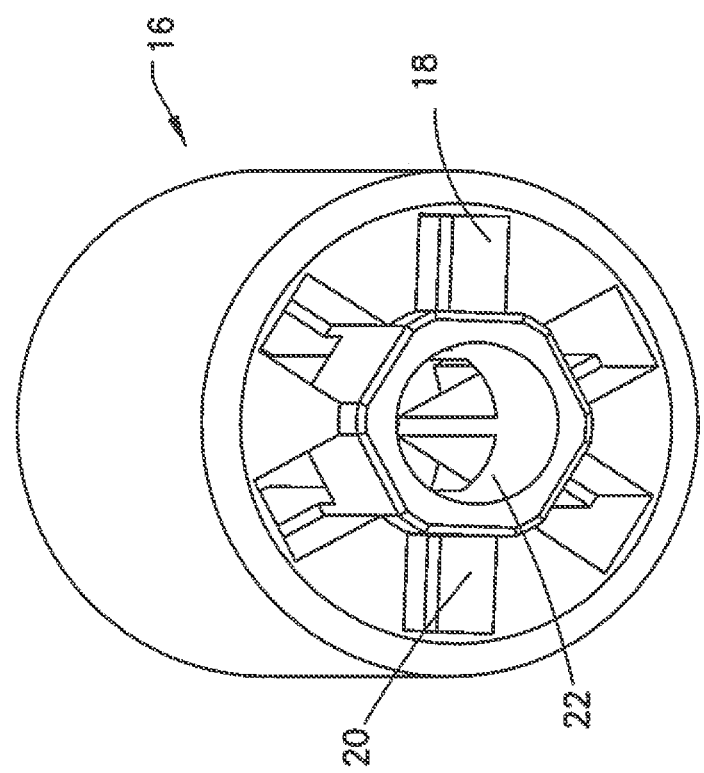
FIG. 14 illustrates a bottom perspective view of the main housing.

The needle assembly 2, according to one embodiment, further includes the main housing 16. As illustrated in FIGS. 12-14, the main housing 16 includes a top cavity 17, a bottom cavity 18, a plurality of openings 20 and a central bottom opening 22. The top cavity 17 supports and encloses the needle hub 10 and the medication delivery pen 4. On the other hand, the bottom cavity 18 supports the remaining components of the needle assembly 2 as described below. FIG. 14 illustrates a bottom view of the main housing 16 including the plurality of openings 20 each enclosing one of the plurality of needles 34. The bottom view of the main housing 16 also includes a central bottom opening 22 that encloses a sealing septum 60 (needle assembly septum).

According to one embodiment, the proximal end 36 of the plurality of needles 34 in the needle assembly 2 pierces the reservoir septum 6 when the medication delivery pen 4 and the needle assembly 2 are assembled together. In a first position of the needle assembly 2, all of the plurality of needles 34 pierce the reservoir septum 6 and none of the needles are exposed for medication delivery. Specifically, the proximal end 36 of each of the plurality of needles 34 is disposed in the reservoir and a sharpened distal end of each of the plurality of needles 34 is disposed in the sealing septum 60. In a second position of the needle assembly 2, at least one of the plurality of needles 34 is exposed for medicament delivery. Specifically, a sharpened distal end 44 of a selected needle 40 pierces the sealing septum 60. A proximal end 42 of the selected needle 40 continues to pierce the reservoir septum 6. The second position of the needle assembly 2 is described in more detail below.

Figure 15:
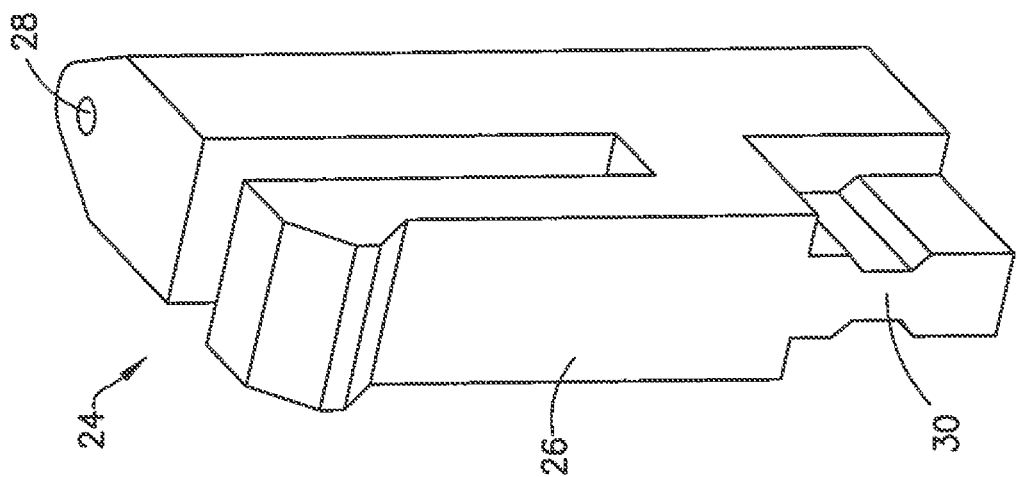
FIG. 15 illustrates a right perspective view of a needle post.

Each of the plurality of needles 34 is fixed to a needle post 24. According to one embodiment, FIG. 15 illustrates the needle post 24 including a needle post flange 26, a hole 28 and a connecting member 30. The needle post flange 26 provides a means to secure the needle post flange 26 to the bottom cavity 18 of the main housing 16. Specifically, the bottom cavity 18 engages the needle post flange 26 between a top and a bottom position. The first position of the needle assembly 2 is configured such that all of the plurality of needle posts 24 is in the top position. The second position of the needle assembly 2 is configured such that the selected needle 40 of the plurality of needles 34 is disposed in the bottom position.

Each of the plurality of needles 34 is fixed to a respective hole 28 in the needle post 24 via an adhesive or a press fit, for example. The plurality of connecting members 30 is disposed at a bottom portion of each of the plurality of needle posts 24. Each of the plurality of connecting members 30 is configured to engage one of the plurality of integrated peel tabs 70.

According to one embodiment, the sealing septum (needle assembly septum) 60 is disposed in the central bottom opening 22 of the main housing 16. The sealing septum 60 is configured to seal and sterilize the plurality of needles 34 when the plurality of needles 34 is not in use. Specifically, when the needle assembly 2 is in the first position, the sharpened distal end of the plurality of needles 34 is disposed in the sealing septum 60. When the needle assembly 2 is in the second positon, a sharpened distal end 44 of the selected needle 40 of the plurality of needles 34 pierces the sealing septum 60 and is exposed for medicament delivery. The sealing septum 60 stores each of the plurality of needles 34 in a sterile environment prior to use and improves safety by protecting a user from inadvertent contact.

Figure 16:
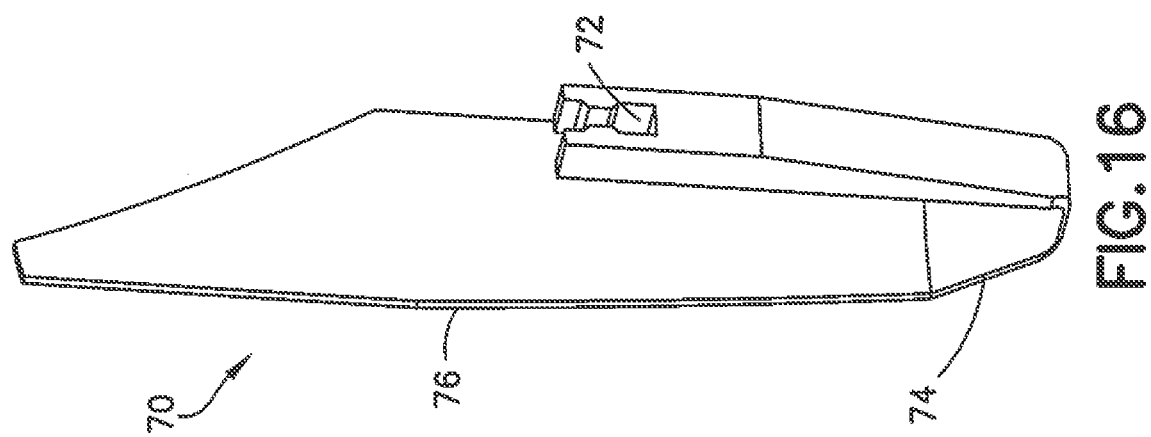
FIG. 16 illustrates a left perspective view of an integrated peel tab.

According to one embodiment, FIG. 16 illustrates that each of the plurality of integrated peel tabs 70 includes a connector portion 72, a bent portion 74 and a peel portion 76. The plurality of integrated peel tabs 70 comprises a flexible laminate such as a Tyvek-like material or a thinly molded plastic. The connector portion 72 of each of the plurality of integrated peel tabs 70 is disposed in the main housing 16 and is configured to be releasably connected to the connecting member 30 of each of the plurality of needle posts 24. Preferably, the engagement between the connector portion 72 and the connecting member 30 is an annular snap fit, although other connecting means such as an interference fit are contemplated.

The bent portion 74 of each of the plurality of integrated peel tabs 70 flexibly bends around a bottom surface of the main housing 16 and enters into the main housing 16 as illustrated in FIG. 3. The user is able to unbend the bent portion 74 when removing one of the integrated peel tabs 70 from the needle assembly 2. The peel portion 76 wraps around an outer surface of the main housing 16 to be easily accessible to the user. Preferably, the peel portion 76 is removably attached to the main housing 16 by an adhesive.

Figure 4:
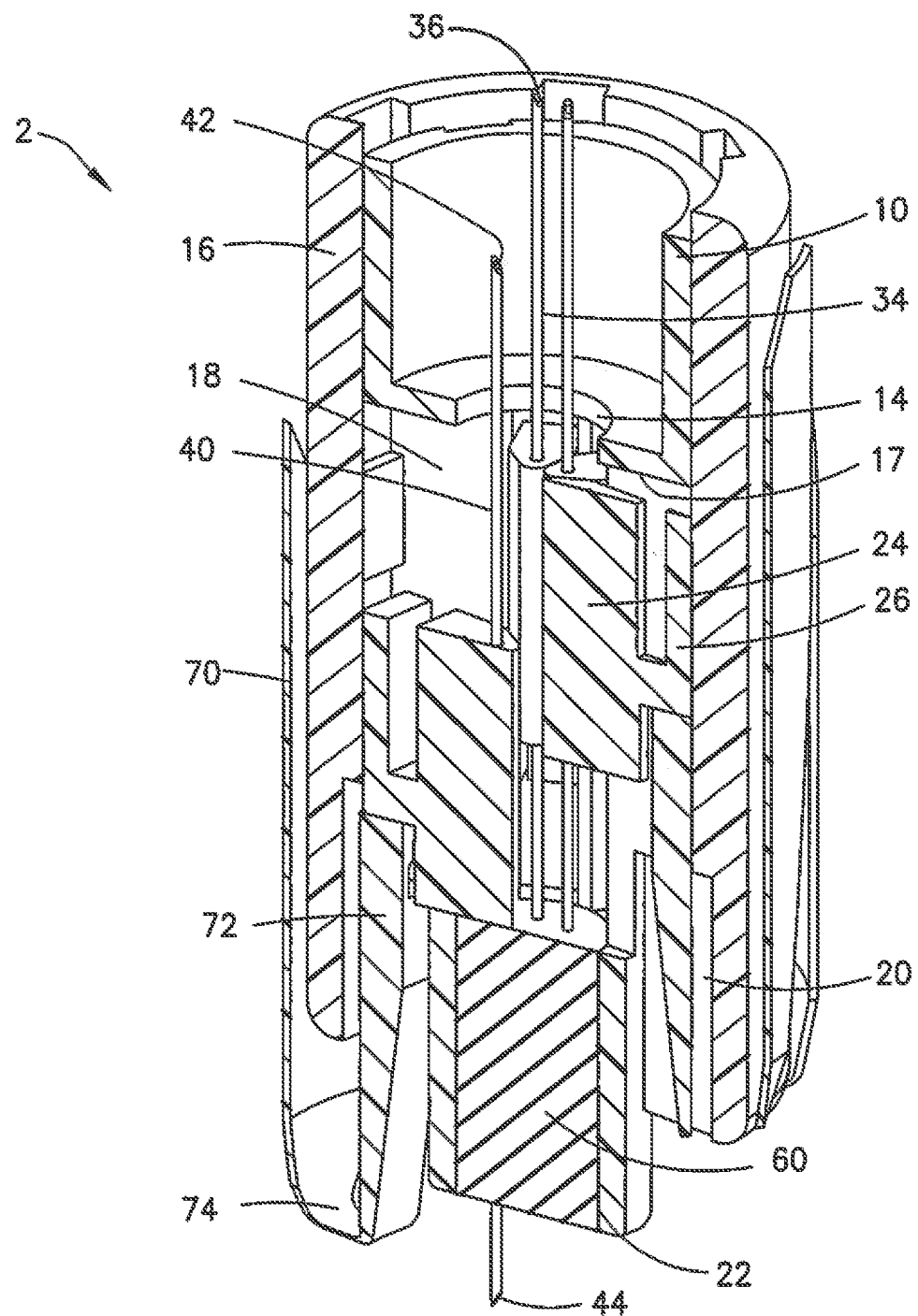
FIG. 4 illustrates a cross sectional view of a second position of the needle assembly with a plurality of peel tabs.

The operation of the needle assembly 2 is now explained as follows. According to one embodiment, when the user desires to fluidly connect the needle assembly 2 to the medication delivery pen 4 for use, the user unwraps one of the plurality of peel tabs 70 from the outer surface of the main housing 16. The user draws one of the plurality of peel tabs 70 out of the main housing 16 and pulls it downward. Typically, the user unbends the bent portion 74 of the peel tab 70 for removal from the main housing 16. This causes one of the plurality of needle posts 24 that is fixed to the selected needle 40 to move downward as illustrated in FIG. 4. The needle post 24 fixed to the selected needle 40 moves from the top position to the bottom position and contacts a top surface of the sealing septum 60. Thus, FIG. 4 illustrates the needle assembly 2 in the second position.

Figure 5:
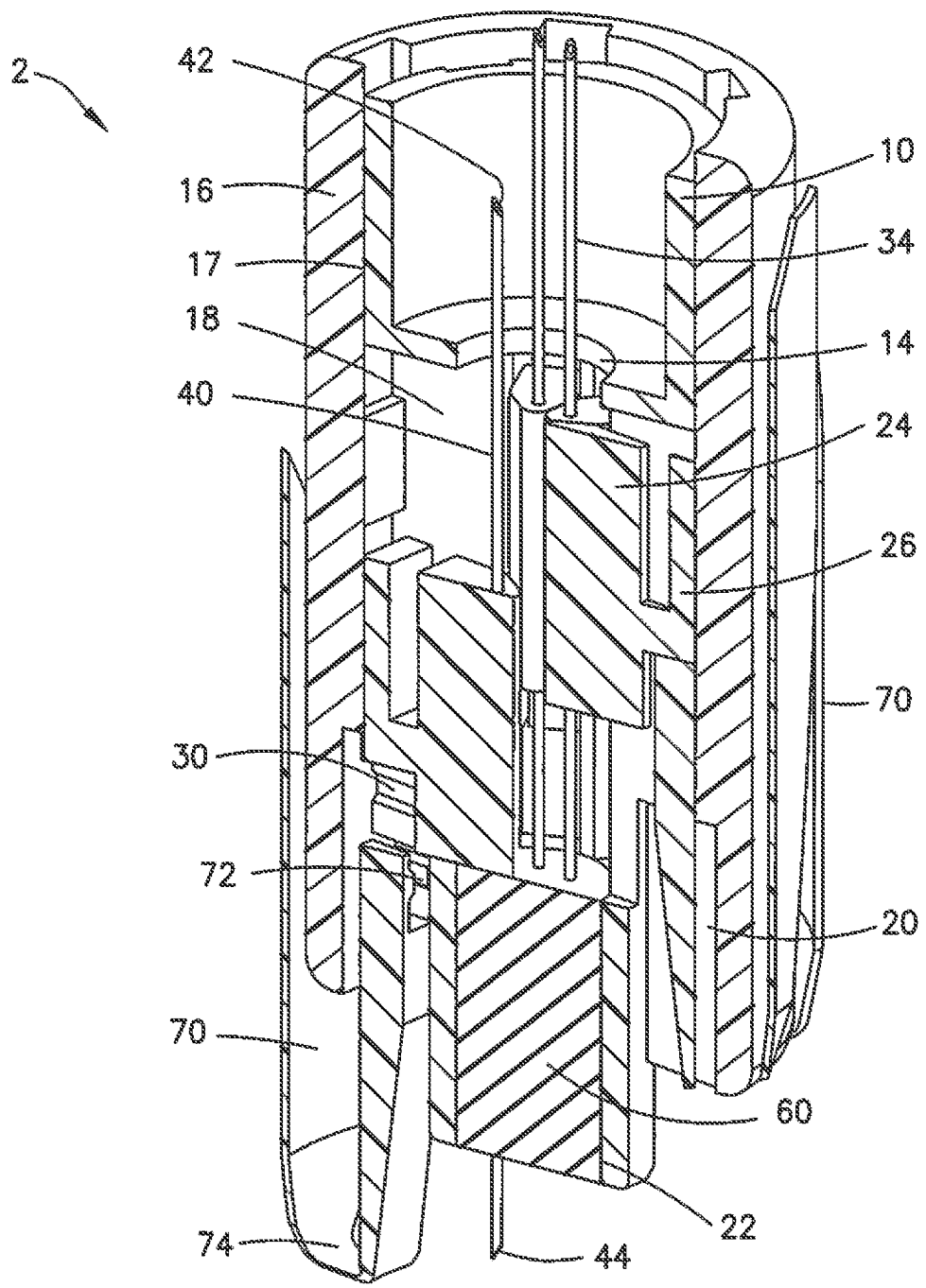
FIG. 5 illustrates a cross sectional view of the second position of the needle assembly with a peel tab being removed.
Figure 6:
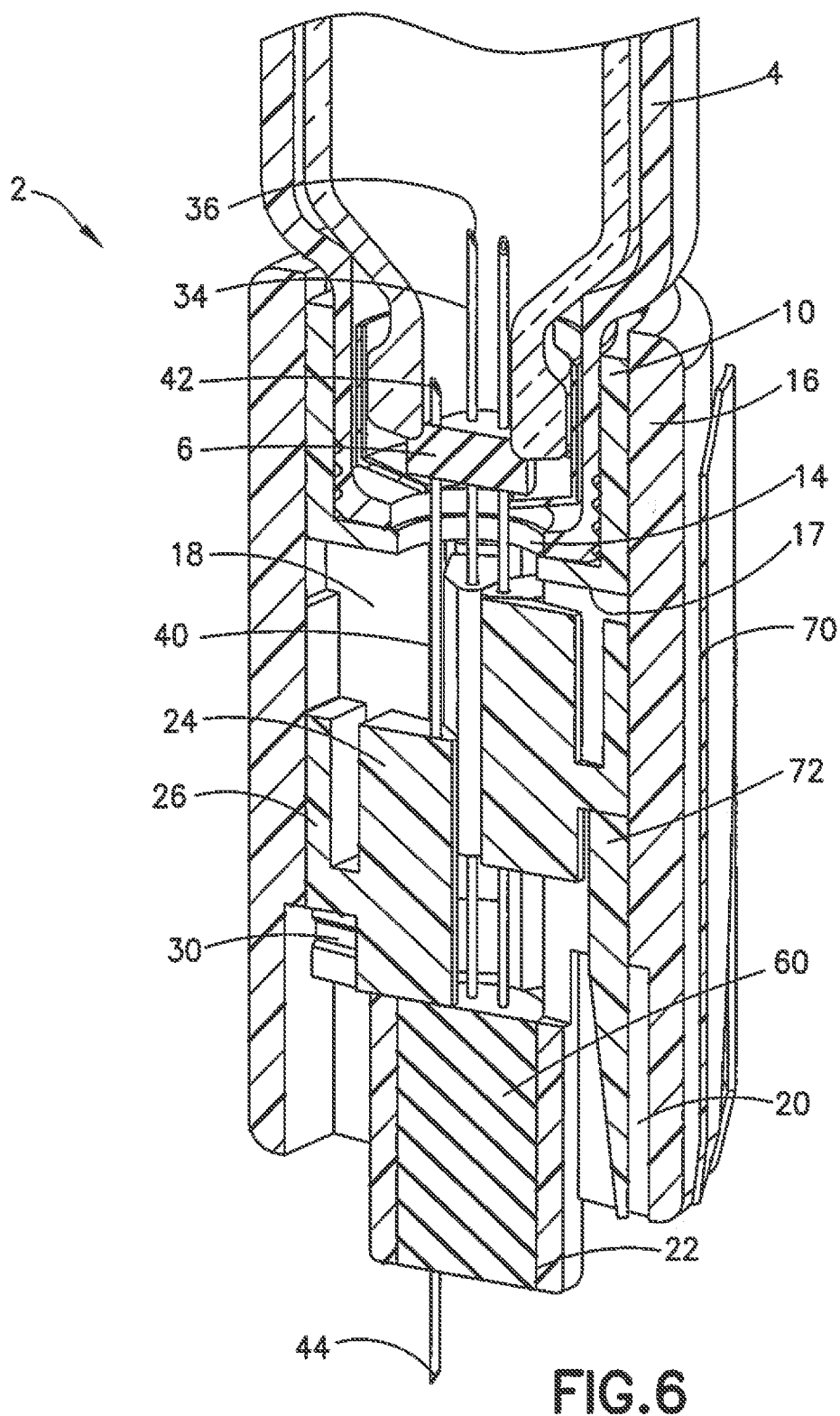
FIG. 6 illustrates a cross sectional view of the second position of the needle assembly.

FIG. 5 illustrates the peel tab 70 of the selected needle 40 being removed in the second position of the needle assembly 2. Specifically, the user pulls the connector portion 72 of the peel tab 70 downward and away from the needle assembly 2. This downward force disengages the annular snap fit, for example, between the connector portion 72 and the connecting member 30 of the needle post 24. Subsequently, as illustrated in FIG. 6, the peel tab 70 of the selected needle 40 is discarded by the user. The selected needle 40 is exposed and ready for medicament delivery.

When the needle assembly 2 is in the second position, the distal end 44 of the selected needle 40 is exposed for medication delivery. Although the selected needle 40 moves downward, the proximal end 42 of the selected needle 40 continues to pierce the reservoir septum 6 of the medication deliver pen 4. Thus, the proximal end 42 of the selected needle 40 remains in fluid communication with the reservoir of the medication delivery pen 4. Accordingly, medicament is received at the proximal end 42 of the selected needle 40 and exits the distal end 44 to be delivered to a patient.

While the needle assembly 2 is in the second position, a remaining plurality of needles 34 (not including the selected needle 40) and the associated needle post 24 remain in the top position. Specifically, the proximal ends 36 of the remaining plurality of needles 34 continue to pierce the reservoir septum 6. However, the distal ends of the remaining plurality of needles 34 are sealed by the sealing septum 60. Thus, the remaining plurality of needles 34 is not available for medication delivery.

Figure 7:
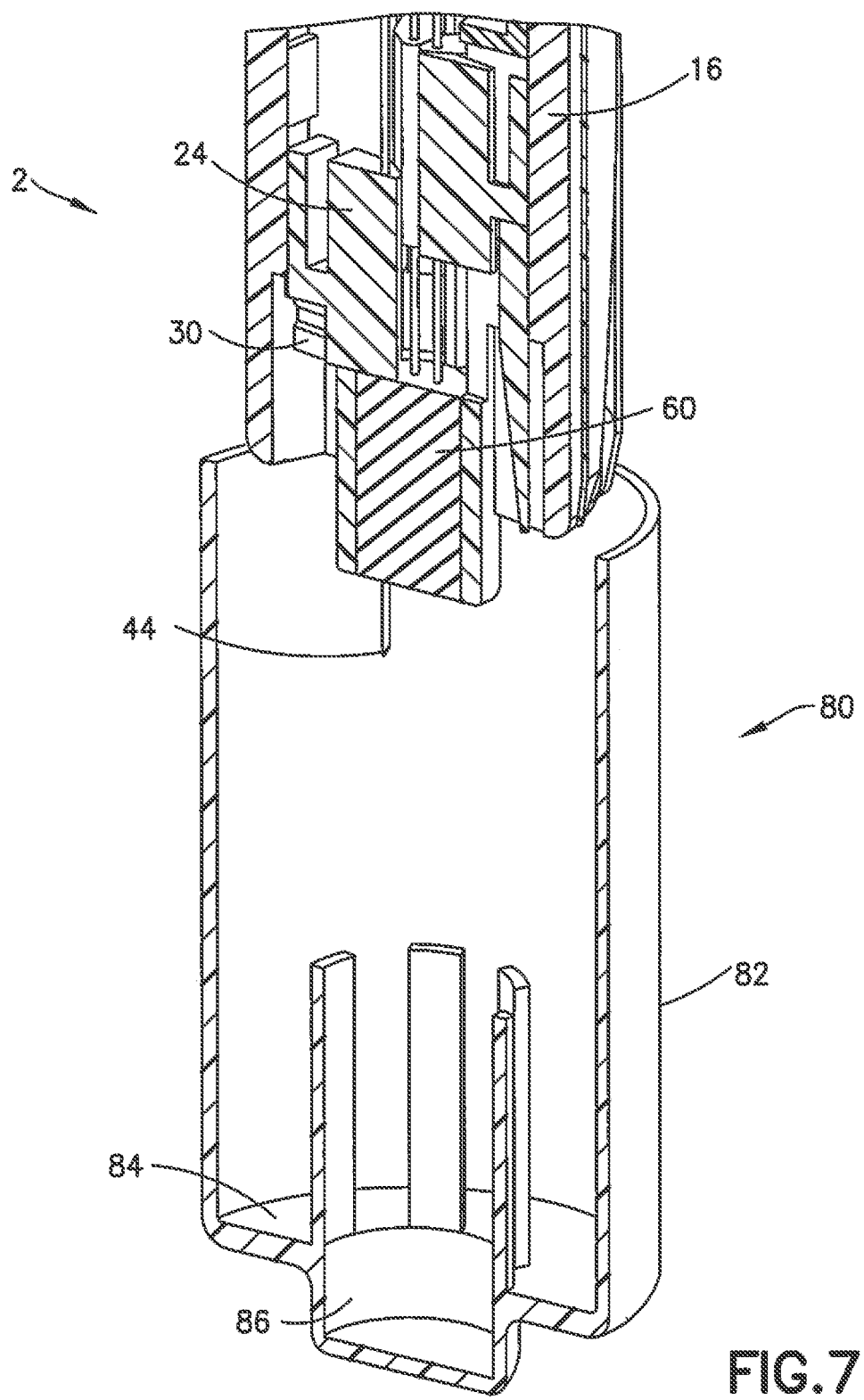
FIG. 7 illustrates a cross sectional view of the second position of the needle assembly with the cover being assembled.

According to one embodiment, FIG. 7 illustrates the cover 80 used to move the needle assembly 2 from the second position to the first position. The cover 80 includes a cylinder 82, a base 84 and a hollow protrusion 86. The cylinder 82 surrounds and protects the needle assembly 2 when not in use. The base 84 covers a bottom surface of the main housing 16 of the needle assembly 2 and prevents tampering. The hollow protrusion 86 is a slotted wall without an opening at the base 84. The slotted wall 86 extends from the base 84 and is disposed centrally within the cylinder 82. Each portion of the slotted wall 86 surrounds the sealing septum 60 and enters into one of the plurality of openings 20 in the main housing 16. When the cover 80 is placed on the needle assembly 2, the protrusion 86 applies pressure by pushing the needle post connecting member 30 of the needle post 24 of the selected needle 40 from the bottom position to the top position.

Figure 8:
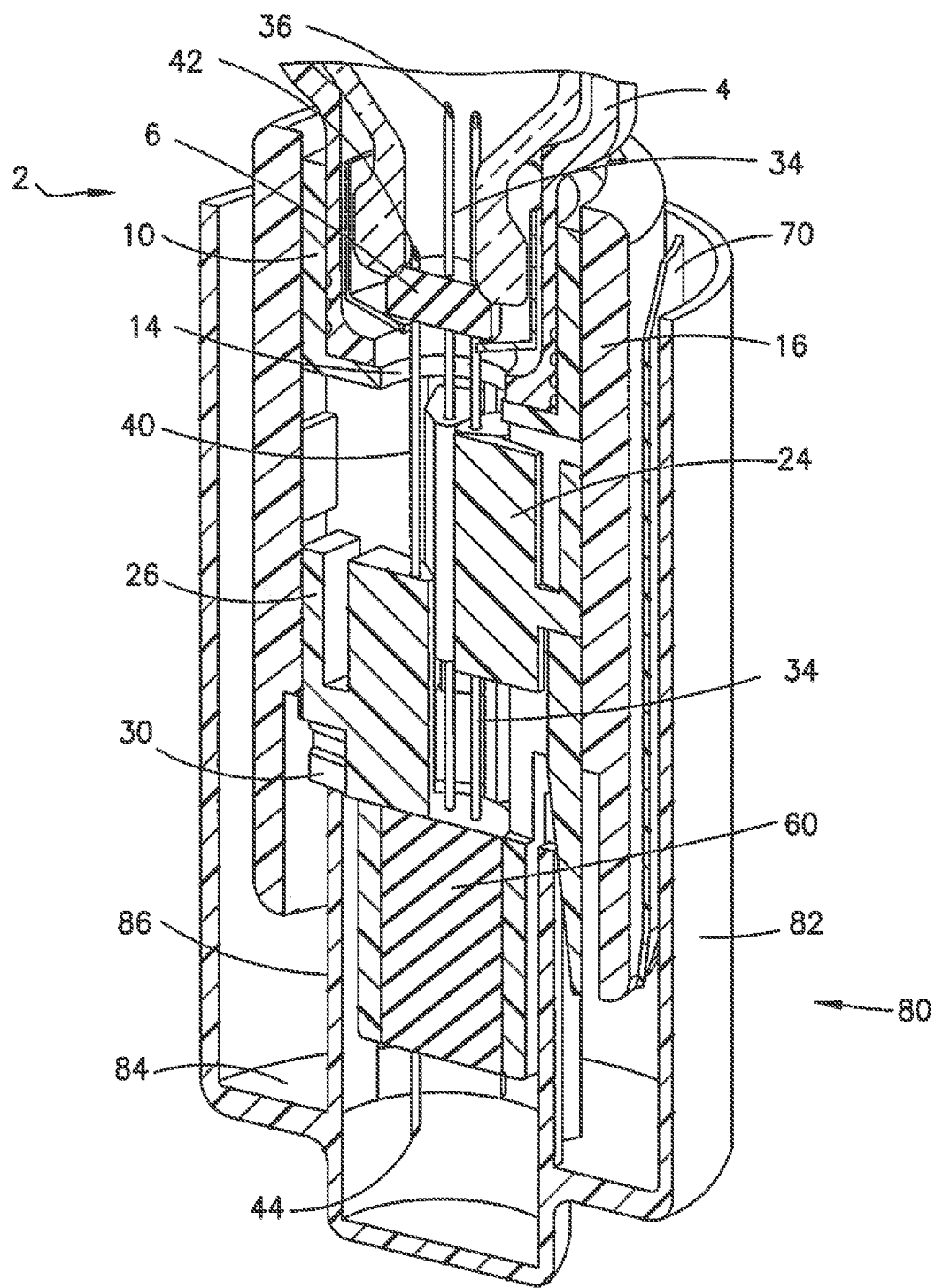
FIG. 8 illustrates a cross sectional view of the second position of the needle assembly with the cover contacting a needle post.
Figure 9:
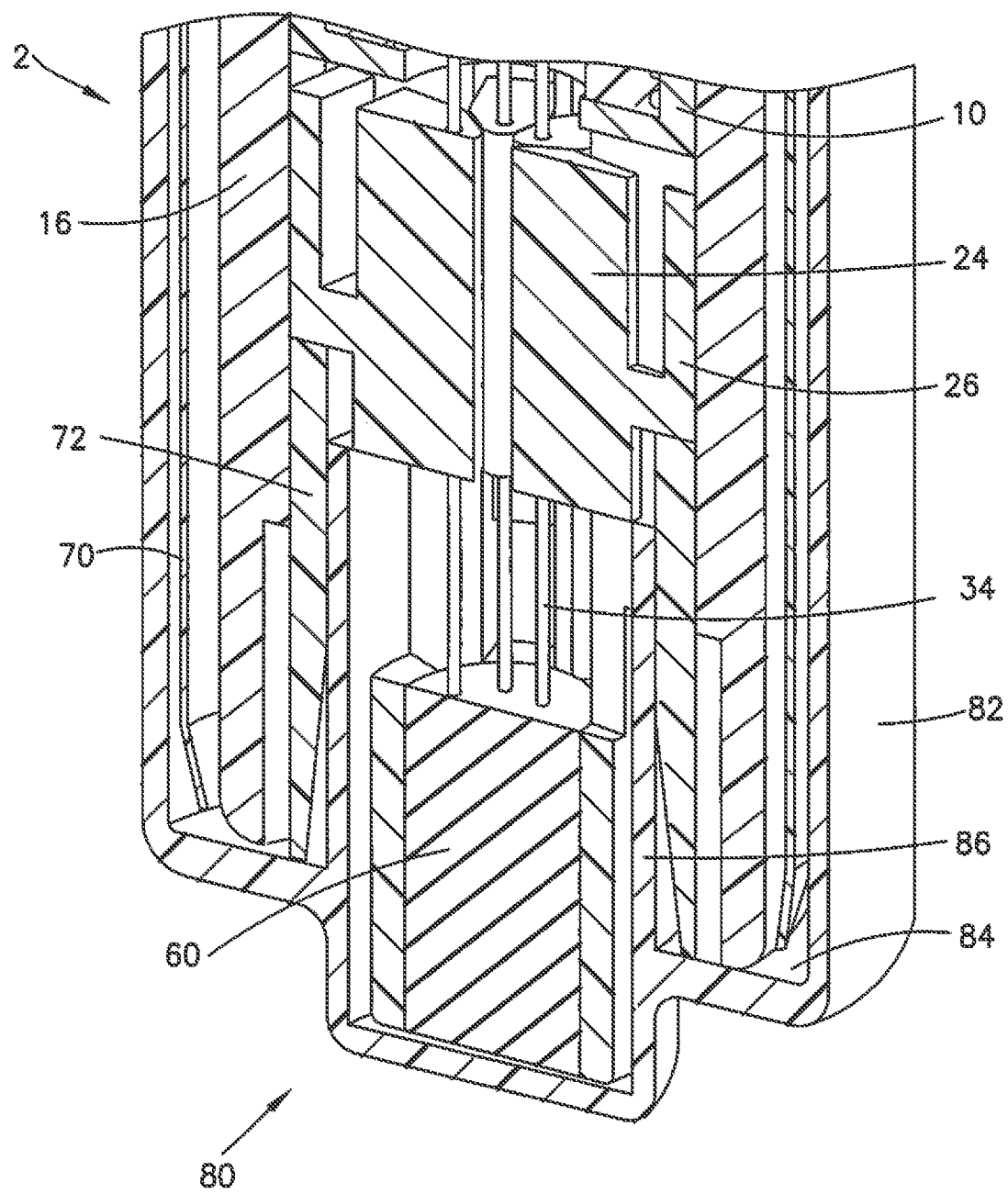
FIG. 9 illustrates a cross sectional view of the first position of the needle assembly with the cover pushing the needle post to a top position.
Figure 10:
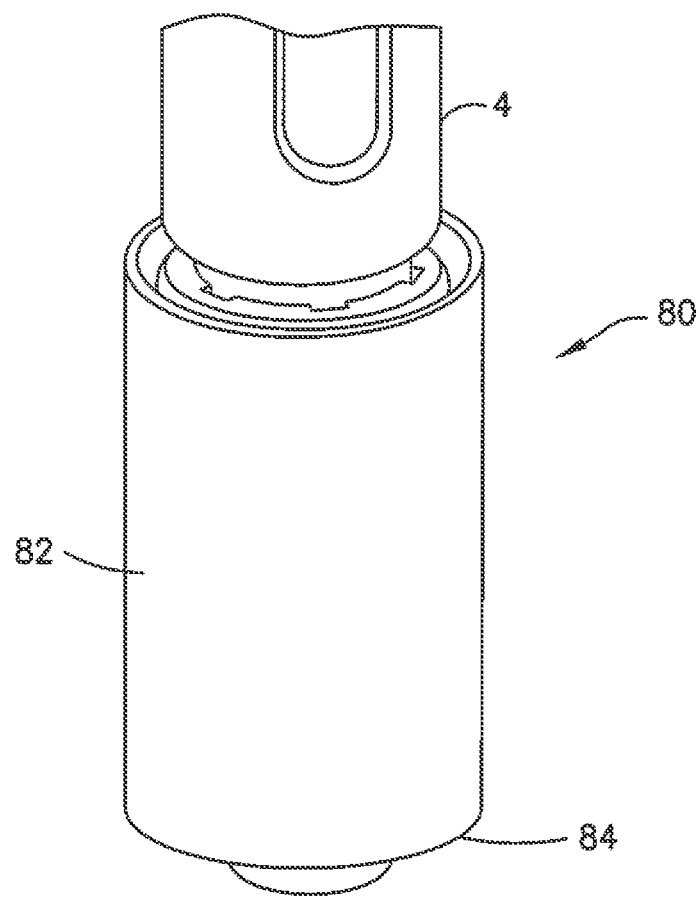
FIG. 10 illustrates a front elevation view of the cover assembled on the needle assembly.

According to one embodiment, FIGS. 8-10 illustrate the protrusion 86 of the cover 80 moving the needle post 24 by applying pressure to the needle post connecting member 30. FIG. 8 illustrates the second position of the needle assembly 2, FIG. 9 illustrates the first position of the needle assembly 2, and FIG. 10 illustrates a perspective view of the needle assembly 2 in the first position. These figures also illustrate that the plurality of needle posts 24 is arranged with respect to a central axis of the main housing 16 such that each of the connecting members 30 radially extends beyond the sealing septum 60. Such a configuration advantageously allows the protrusion 86 of the cover 80 to contact each of the connecting members 30 of the plurality of needle posts 24 during each successive use of the plurality of needles 34.

According to one embodiment, after the needle assembly 2 is returned to the first position, as illustrated in FIG. 10, the selected needle 40 can no longer be used. Since the integrated peel tab 70 of the selected needle 40 is removed by the user, there is no means to move the selected needle 40 into the second position of the needle assembly 2. That is, the connector portion 72 of the integrated peel tab 70 is no longer connected to the integrated peel tab 60. Thus, the user cannot reuse the needle by moving the respective needle post 24 of the selected needle 40 from the top position to the bottom position.

After the needle assembly 2 is returned to the first position, according to one embodiment, an adjacent needle is selected for use. Specifically, as illustrated in FIG. 2, the plurality of integrated peel tabs 70 is arranged consecutively around the outer surface of the main housing 16. The plurality of integrated peel tabs 70 do not overlap with each other. Although the adjacent peel tab 70 should be used, any of the remaining plurality of integrated peel tabs 70 can be used.

To continue operation of the needle assembly 2, the user pulls a peel tab of the plurality of peel tabs 70 to cause the selected needle 40 to move from the first position to the second position of the needle assembly as described above. The selected peel tab is removed and the needle assembly 2 is ready for medication delivery. After use, the user places the cover 80 over the needle assembly 2 and returns the selected needle 40 to the first position of the needle assembly 2. The needle assembly 2 is now ready for another needle to be used. These steps are repeated until all of the plurality of needles 34 is used.

During operation, although the selected needle 40 moves axially, the selected needle 40 does not move radially. In fact, none of the plurality of needles 34 substantially moves radially or rotates at any point during operation. No substantial radial or rotational movement in this regard is understood as 0±5% with respect to a center axis of the needle assembly 2. Preferably, one skilled in the art understands that substantial in this context means that no radial of rotational movement is required to perform the intended function. Slight radial or rotational movement is desired to ensure the proper spacing of parts for smooth operation and proper movement of the needles axially without jamming.

Each of the plurality of needles 34 is advantageously in fluid communication with the reservoir of the medication delivery pen 4 throughout the operation of the needle assembly 2. Specifically, the plurality of needles 34 pierces the reservoir septum 6 of the medication delivery pen 4 when the needle assembly 2 is connected to the medication delivery pen 4. Such an arrangement advantageously provides simplicity in design and improves sterility.

Figure 17:
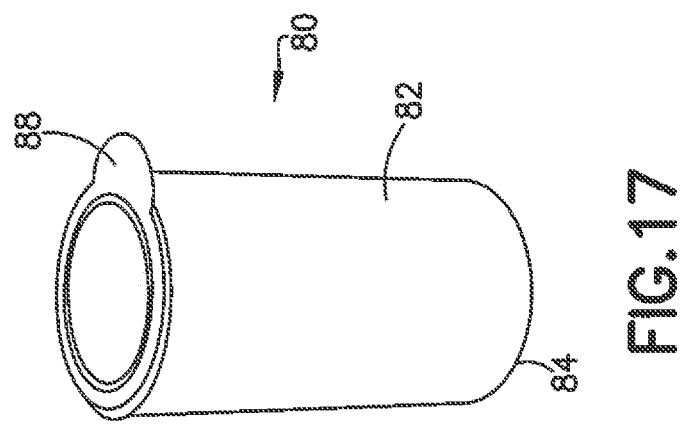
FIG. 17 illustrates a right perspective view of the needle assembly in the cover and sealed by a teardrop label.

According to one embodiment, FIG. 17 illustrates the cover 80 enclosing the needle assembly 2. The cover 80 is sealed with a teardrop label 88 to seal the needle assembly 2 and maintain its sterility for transportation and security purposes prior to operating with the medication delivery pen 4. When the needle assembly 2 is ready for use, the user peels off the teardrop label 88 and removes the needle assembly 2 from the cover 80.

The foregoing detailed description of the certain exemplary embodiments has been provided for the purpose of explaining the principles of the invention and its practical application, thereby enabling others skilled in the art to understand the invention for various embodiments and with various modifications as are suited to the particular use contemplated. This description is not necessarily intended to be exhaustive or to limit the invention to the precise embodiments disclosed. Any of the embodiments and/or elements disclosed herein may be combined with one another to form various additional embodiments not specifically disclosed, as long as they do not contradict each other. Accordingly, additional embodiments are possible and are intended to be encompassed within this specification and the scope of the invention. The specification describes specific examples to accomplish a more general goal that may be accomplished in another way.

As used in this application, the terms "front," "rear," "upper," "lower," "upwardly," "downwardly," and other orientational descriptors are intended to facilitate the description of the exemplary embodiments of the present invention, and are not intended to limit the structure of the exemplary embodiments of the present invention to any particular position or orientation. Terms of degree, such as "substantially" or "approximately" are understood by those of ordinary skill to refer to reasonable ranges outside of the given value, for example, general tolerances associated with manufacturing, assembly, and use of the described embodiments.

The invention claimed is:

1. An attachable needle assembly for use on a medication delivery pen, the needle assembly comprising:
   a housing configured to engage the medication delivery pen, the housing enclosing:
      a plurality of needles configured to pierce a reservoir septum of the medication delivery pen;
      a plurality of needle posts each securing one of the plurality of needles; and
      a needle assembly septum enclosing the plurality of needles; and
   a plurality of integrated peel tabs each detachably connected to one of the plurality of needle posts, wherein
   in a first position of the needle assembly, the plurality of needles is disposed in the needle assembly septum, and in a second position of the needle assembly, one of the plurality of integrated peel tabs is drawn out of the housing to cause a selected needle of the plurality of needles to pierce the needle assembly septum and be exposed for medication delivery.

2. The attachable needle assembly of claim 1, wherein the housing further includes a hub having internal threads that are configured to engage external threads of the medication delivery pen.

3. The attachable needle assembly of claim 2, wherein when the needle assembly is engaged to the medication delivery pen, a proximal end of each of the plurality of needles always pierces the reservoir septum of the medication delivery pen.

4. The attachable needle assembly of claim 1, wherein a distal end of the plurality of needles is disposed in the needle assembly septum in the first position of the needle assembly.

5. The attachable needle assembly of claim 1, wherein a distal end of the selected needle of the plurality of needles pierces the needle assembly septum in the second position of the needle assembly.

6. The attachable needle assembly of claim 1, wherein a distal end of remaining needles of the plurality of needles is disposed in the needle assembly septum in the second position of the needle assembly.

7. The attachable needle assembly of claim 1, wherein the plurality of integrated peel tabs includes at least six peel tabs.

8. The attachable needle assembly of claim 1, wherein the plurality of integrated peel tabs is wrapped around the housing.

9. The attachable needle assembly of claim 8, wherein the plurality of integrated peel tabs is non-overlapping.

10. The attachable needle assembly of claim 1, wherein the plurality of integrated peel tabs is disposed within the housing.

11. The attachable needle assembly of claim 1, wherein each of the plurality of integrated peel tabs is flexibly bent to enter into a bottom surface of the housing.

12. The attachable needle assembly of claim 1, wherein in the second position of the needle assembly, the corresponding peel tab of the selected needle is removed from the needle assembly.

13. The attachable needle assembly of claim 1, wherein each of the plurality of needles is unable to be reused when returned to the first position after use with the respective integrated peel tab removed.

14. The attachable needle assembly of claim 1, wherein the plurality of needles only move axially and does not substantially move radially and does not substantially rotate.

15. The attachable needle assembly of claim 1, further including
   a cover enclosing the needle assembly; and
   a label sealing and maintaining sterility of the needle assembly in the cover prior to operating with the medication delivery pen.

16. The attachable needle assembly of claim 1, wherein a cover is placed over a distal end of the needle assembly to apply pressure to one of the plurality of needle posts to return the selected needle from the second position to the first position of the needle assembly.

17. The attachable needle assembly of claim 1, further comprising:
   a cover including:
      a cylinder;
      a base; and
      a hollow protrusion extending from the base and disposed within the cylinder; wherein
   the hollow protrusion engages the housing to apply pressure to the one of the plurality of needle posts to return the needle assembly from the second position to the first position.

18. A method of assembling an attachable needle assembly and using the attachable needle assembly on a medication delivery pen, the method comprising:
   piercing a reservoir septum of the medication delivery pen with a plurality of needles;

engaging the medication delivery pen with a housing enclosing the plurality of needles;

securing each of the plurality of needles to one of a plurality of needle posts;

disposing the plurality of needles in a needle assembly septum; and connecting a plurality of integrated peel tabs to each of the plurality of needle posts, wherein in a first position of the needle assembly, the plurality of needles is disposed in the needle assembly septum, and in a second position of the needle assembly, one of the plurality of integrated peel tabs is drawn out of the housing to cause a selected needle of the plurality of needles to pierce the needle assembly septum.

* * * * *